United States Patent
Porath et al.

(10) Patent No.: US 9,629,567 B2
(45) Date of Patent: Apr. 25, 2017

(54) MAPPING OF COMPLEX FRACTIONATED ATRIAL ELECTROGRAM

(75) Inventors: Joshua Porath, Haifa (IL); Aharon Abbo, Givat Ada (IL); Aharon Turgeman, Zichron Ya'acov (IL); Koonlawee Nademanee, Encino, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 1921 days.

(21) Appl. No.: 11/620,370

(22) Filed: Jan. 5, 2007

(65) Prior Publication Data

US 2007/0197929 A1    Aug. 23, 2007

Related U.S. Application Data

(60) Provisional application No. 60/758,317, filed on Jan. 12, 2006.

(51) Int. Cl.
| | |
|---|---|
| *A61B 5/04* | (2006.01) |
| *A61B 5/042* | (2006.01) |
| *A61B 5/0452* | (2006.01) |
| *A61B 18/14* | (2006.01) |
| *A61B 18/00* | (2006.01) |

(52) U.S. Cl.
CPC .......... *A61B 5/0422* (2013.01); *A61B 5/0452* (2013.01); *A61B 18/1492* (2013.01); *A61B 2018/00839* (2013.01)

(58) Field of Classification Search
CPC .......................... A61B 5/0422; A61B 5/0452
USPC .............................. 600/509, 523; 70/509, 523
See application file for complete search history.

(56) References Cited

U.S. PATENT DOCUMENTS

| | | |
|---|---|---|
| 5,546,951 A | 8/1996 | Ben-Haim |
| 5,738,096 A | 4/1998 | Ben-Haim |
| 6,226,542 B1 | 5/2001 | Reisfeld |
| 6,301,496 B1 | 10/2001 | Reisfeld |
| 6,332,089 B1 | 12/2001 | Acker et al. |
| 6,618,612 B1 | 9/2003 | Acker et al. |
| 6,669,692 B1 | 12/2003 | Nelson et al. |
| 6,690,963 B2 | 2/2004 | Ben-Haim et al. |

(Continued)

FOREIGN PATENT DOCUMENTS

| | | |
|---|---|---|
| JP | 2006-005907 A | 1/2006 |
| WO | WO 96/05768 A1 | 2/1996 |
| WO | WO 2005/122939 A | 12/2005 |

OTHER PUBLICATIONS

Nademanee, K., MD et al. A New Approach for Catheter Ablation of Atrial Fibrillation: Mapping of the Electrophysiologic Substrate, Journal of American College of Cardiology, vol. 43, No. 11, 2004, pp. 2044-2053.

(Continued)

*Primary Examiner* — Christopher D Koharski
*Assistant Examiner* — Michael D Abreu
(74) *Attorney, Agent, or Firm* — Louis J. Capezzuto

(57) ABSTRACT

Software and apparatus are provided to automatically detect and map areas of complex fractionated electrograms within cardiac chambers. Electrogram signal are analyzed to count the number of complexes whose amplitude and peak-to-peak intervals meet certain criteria. Functional maps indicating average complex interval, shortest complex interval, and confidence levels are produced for display.

22 Claims, 11 Drawing Sheets

(56) References Cited

U.S. PATENT DOCUMENTS

| | | | |
|---|---|---|---|
| 6,892,091 | B1 | 5/2005 | Ben-Haim et al. |
| 2003/0120150 | A1 | 6/2003 | Govari |
| 2003/0120163 | A1 | 6/2003 | Rudy et al. |
| 2004/0068178 | A1 | 4/2004 | Govari |
| 2004/0102769 | A1 | 5/2004 | Schwartz et al. |
| 2004/0147920 | A1 | 7/2004 | Keidar |
| 2005/0099290 | A1 | 5/2005 | Govari |
| 2007/0073179 | A1* | 3/2007 | Afonso et al. ............... 600/523 |
| 2007/0208260 | A1 | 9/2007 | Afonso |

OTHER PUBLICATIONS

Nademanee et al: "How to Perform Electrogram-guided Atrial Fibrillation Ablation"; Heart Rhythm, Aug. 2006; pp. 981-984; vol. 3 No. 8, Elsevier, NL.

Sethi et al: "Mapping Complex Fractionated Electrograms and Dominant Frequencies Using the NavX Navigation System During Atrial Fibrillation Ablation"; Heart Rhythm, May 2006; p. S60; vol. 3, No. 5.

Search Report No. EP 07 25 0104 dated Oct. 31, 2007.

Arora, R. et al. Neural Substrate for Atrial Fibrillation: Implications for Targeted Parasympathetic Blockade in the Posterior Left Atrium. Am J Physiol Heart Circ Physiol, 2008;294:H134-H144.

Atienza, F. et al. Mechanisms of Fractionated Electrograms Formation in the Posterior Left Atrium During Paroxysmal Atrial Fibrillation in Humans. J. Am. Coll. Cardiol. 2011;57;1081-1092.

Calo, L. et al. Diagnostic Accuracy of a New Software for Complex Fractionated Electrograms Identification in Patients With Persistent and Permanent Atrial Fibrillation. J Cardiovasc Electrophysiol. 2008;1-7.

Duytschaever, M. et al. A Meta-Analysis on Adjunctive Complex Fractionated Atrial Electrogram Ablation: Comparing the Incomparable? Europace 2011;13;909-910.

Estner, H.L. et al. Electrogram-Guided Substrate Ablation With or Without Pulmonary Vein Isolation in Patients With Persistent Atrial Fibrillation. Europace 2008;10;1281-1287.

Ghias, M.,MD et al. The Role of Ganglionated Plexi in Apnea-Related Atrial Fibrillation. Journal of the American College of Cardiology 2009; 54; 22:2075-2083.

Hou, Y. et al. Ganglionated Plexi Modulate Extrinsic Cardiac Autonomic Nerve Input. Journal of the American College of Cardiology, 2007;50;1;61-68.

Hou, Y. et al. The Interactive Atrial Neural Network: Determining the Connections Between Ganglionated Plexi. Heart Rhythm, 2006;4;1:56-63.

Jacquemet, V. et al. Genesis of Complex Fractionated Atrial Electrograms in Zones of Slow Conduction: A Computer Model of Microfibrosis. Heart Rhythm, 2009;6;6:803-810.

Katritsis, D. et al. Anatomic Approach for Ganglionic Plexi Ablation in Patients With Paroxysmal Atrial Fibrillation. American Journal of Cardiology; 2008;102:330-334.

Kim, A.M. et al. Microfibrosis and Complex Fractionated Atrial Electrograms. Heart Rhythm, 2009;6;6:811-812.

Kong, M.H. et al. Efficacy of Adjunctive Ablation of Complex Fractionated Atrial Electrograms and Pulmonary Vein Isolation for the Treatment of Atrial Fibrillation: A Meta-Analysis of Randomized Controlled Trials. Europace, 2011;13:193-204.

Lemery, R. How to Perform Ablation of the Parasympathetic Ganglia on the Left Atrium, 2006;3;10:1237-1239.

Mikhaylov, E. et al. Outcome of Anatomic Ganglionated Plexi Ablation to Treat Paroxysmal Atrial Fibrillation: A 3-Year Follow-Up Study. Europace, 2010;1-9.

Nademanee, K. et al. Clinical Outcomes of Catheter Substrate Ablation for High-Risk Patients With Atrial Fibrillation. Journal of the American College of Cardiology, 2008;51;8:843-849.

Nattel, S., M.D. Complex Fractionated Atrial Electrograms: Can They Be Made Simple? Heart Rhythm, 2008;5;6:855-856.

Oral, H. M.D. et al. A Randomized Assessment of the Incremental Role of Ablation of Complex Fractionated Atrial Electrograms After Antral Pulmonary Vein Isolation for Long-Lasting Persistent Atrial Fibrillation. Journal of the American College of Cardiology, 2009;53;9:782-789.

Pappone, C, PhD, MD et al. Pulmonary Vein Denervation Enhances Long-Term Benefit After Circumferential Ablation for Paroxysmal Atrial Fibrillation. Circulation, 2004;109:r-7-r14.

Pokushalov, E. The Role of Autonomic Denervation During Catheter Ablation of Atrial Fibrillation. Current Opinion in Cardiology, 2008;23:55-59.

Ru-Hong, J. et al. Regional Ganglionated Plexus Ablation Elimated Rapid Firing in an Electrocally Isolated Pulmonary Vein. Wiley Periodicals, Inc., PACE, 2011:1-4.

Schauerte, P., M.D. et al. Catheter Ablation of Cardiac Autonomic Nerves for Prevention of Vagal Atrial Fibrillation. Circulation, 2000;102:2774-2780.

Verma, A., M.D. et al. Selective CFAE Targeting for Atrial Fibrillation Study (Select AF): Clinical Rationale, Design, and Implementation. J Cardiovasc Electrophysiol, 2010:1-7.

Zhou, J., M.D. et al. Gradients of Atrial Refractoriness and Inducibility of Atrial Fibrillation Due to Stimulation of Ganglionated Plexi. J Cardiovasc Electrophysiol 2007;18:1-8.

Koonlawee, N., et al., "A New Approach for Catheter Ablation of Atrial Fibrillation: Mapping of the Electrophysiologic Substrate", Journal of the American College of Cardiology, vol. 43, No. 11, pp. 2044-2053 (2004).

Notification of Reasons for Refusal dated Jan. 22, 2013 for corresponding Japanese Patent Application No. 2007-003735.

\* cited by examiner

FIG. 11

| Point List | | | | | | | |
|---|---|---|---|---|---|---|---|
| Point 146 | | 148 | 150 | | | | |
| # | SCI | ICL | CLT | Tag | Type | Com | In |
| 77 | 70 | 8 | High | | | | |
| 78 | 77 | 4 | | | | | |
| 79 | N/A | 0 | | | | | |
| 80 | 73 | 3 | | | | | |
| 81 | 72 | 6 | Medium | | | | |
| 82 | 76 | 3 | | | | | |
| 83 | N/A | 0 | | | | | |
| 84 | 75 | 12 | High | | | | |
| 85 | 70 | 8 | High | | | | |
| 86 | 70 | 7 | Medium | | | | |
| 87 | 84 | 4 | | | | | |
| 88 | 72 | 4 | | | | | |
| 89 | 83 | 5 | Medium | | | | |
| 90 | 117 | 1 | | | | | |
| 91 | 98 | 3 | | | | | |
| 92 | 76 | 8 | High | | | | |
| 93 | 74 | 11 | High | | | | |
| 94 | 87 | 8 | High | | | | |

MAPPING OF COMPLEX FRACTIONATED ATRIAL ELECTROGRAM

This Application claims the benefit of Provisional Application No. 60/758,317, entitled "Mapping of Complex Fractionated Atrial Electrogram", filed 12 Jan. 2006, which is herein incorporated by reference.

BACKGROUND OF THE INVENTION

Field of the Invention

This invention relates to the diagnosis and treatment of cardiac arrhythmias. More particularly, this invention relates to obtaining information indicative of regional electrical activity in the cardiac chambers, and to the identification and treatment of arrhythmogenic areas.

Description of the Related Art

Cardiac arrhythmias such as atrial fibrillation are an important cause of morbidity and death. Commonly assigned U.S. Pat. Nos. 5,546,951, and 6,690,963, both issued to Ben Haim; and PCT application WO 96/05768, all of which are incorporated herein by reference, disclose methods for sensing an electrical property of heart tissue, for example, local activation time, as a function of the precise location within the heart. Data are acquired with one or more catheters having electrical and location sensors in their distal tips, which are advanced into the heart. Methods of creating a map of the electrical activity of the heart based on these data are disclosed in commonly assigned U.S. Pat. Nos. 6,226,542, and 6,301,496, both issued to Reisfeld, which are incorporated herein by reference. As indicated in these patents, location and electrical activity is typically initially measured on about 10 to about 20 points on the interior surface of the heart. These data points are then generally sufficient to generate a preliminary reconstruction or map of the cardiac surface. The preliminary map is often combined with data taken at additional points in order to generate a more comprehensive map of the heart's electrical activity. Indeed, in clinical settings, it is not uncommon to accumulate data at 100 or more sites to generate a detailed, comprehensive map of heart chamber electrical activity. The generated detailed map may then serve as the basis for deciding on a therapeutic course of action, for example, tissue ablation, to alter the propagation of the heart's electrical activity and to restore normal heart rhythm.

Catheters containing position sensors may be used to determine the trajectory of points on the cardiac surface. These trajectories may be used to infer motion characteristics such as the contractility of the tissue. As disclosed in U.S. Pat. No. 5,738,096, issued to Ben Haim, which is incorporated herein in its entirety by reference, maps depicting such motion characteristics may be constructed when the trajectory information is sampled at a sufficient number of points in the heart.

Electrical activity at a point in the heart is typically measured by advancing a catheter containing an electrical sensor at or near its distal tip to that point in the heart, contacting the tissue with the sensor and acquiring data at that point. One drawback with mapping a cardiac chamber using a catheter containing only a single, distal tip electrode is the long period of time required to accumulate data on a point-by-point basis over the requisite number of points required for a detailed map of the chamber as a whole. Accordingly, multiple-electrode catheters have been developed to simultaneously measure electrical activity at multiple points in the heart chamber.

Over the past decade, several mapping studies in human atrial fibrillation have made the following important observations. Atrial electrograms during sustained atrial fibrillation have three distinct patterns: single potential, double potential and a complex fractionated atrial electrograms (CFAE's). The CFAE areas represent the atrial fibrillation substrate sites and become important target sites for ablation. By ablating areas having persistent CFAE's, atrial fibrillation may be eliminated and even rendered non-inducible.

In the document *A New Approach for Catheter Ablation of Atrial Fibrillation: Mapping of the Electrophysiologic Substrate*, Nademanee et al., J. Am. Coll. Cardiol., 2004; 43(11): 2044-2053, it is proposed that atrial fibrillation may be successfully treated by ablating sites exhibiting a complex fractionated atrial electrogram. The authors identified areas of CFAE during atrial fibrillation, and then applied radiofrequency ablation to these areas. As a result of the ablation, the atrial fibrillation was resolved in the large majority of the cases.

In the above-noted study of Nademanee et al., CFAE was mapped manually, i.e., the actual local electrogram was read out during atrial fibrillation, and a human operator read the electrogram to identify sites of CFAE. The operator marked these sites on an electrical activation map as points of reference for subsequent ablation.

SUMMARY OF THE INVENTION

There is a need for an automatic process that can locate and map areas of CFAE without intervention by an expert human operator. In response to this need, aspects of the present invention provide specialized system software and systems for electroanatomical mapping systems, in order to map areas of CFAE automatically within cardiac chambers. A method developed for this purpose analyzes the electrogram signal to count the number of CFAE complexes whose amplitude and peak-to-peak intervals meet certain criteria.

An embodiment of the invention provides a method for mapping abnormal electrical activity in a heart of a living subject, which is carried out by obtaining electrical signal data from respective locations of the heart, automatically analyzing the signal data to identify complex fractionated electrograms therein, and displaying information derived from the signal data indicative of a spatial distribution of the complex fractionated electrograms in the heart.

According to am aspect of the method, automatic analysis of the signal data includes identifying voltage peaks having amplitudes within a predefined voltage range, and identifying peak-to-peak intervals between the identified voltage peaks that occur within a predefined time range.

In another aspect of the method, the electrical signals are obtained by contacting a surface of the heart using a catheter having an electrode and a position sensor distally disposed thereon, measuring electrical signals via the electrode at the respective locations, and determining location information from the position sensor from at least one point on the surface. The electrical signals may be measured using a unipolar or a bipolar electrode. The cardiac surface can be an endocardial surface or an epicardial surface. The locations may be in an atrium or a ventricle of the heart.

In another aspect of the method, electrical signal data are obtained from the respective locations of the heart by disposing multiple electrodes on an external surface of the subject, detecting electrical signals from the heart using the multiple electrodes, and applying values of the electrical signals to a pre-established impedance matrix to identify the respective locations.

According to one aspect of the method, displaying information includes constructing a functional map of the heart. The map may be coded according to average durations of the complex fractionated electrograms, shortest complex durations of the complex fractionated electrograms, or according to numbers of the complex fractionated electrograms detected in the respective locations.

Another aspect of the method includes ablating cardiac tissue associated with the complex fractionated electrograms.

Computer Software Product and Apparatus are also provided for carrying out the method.

BRIEF DESCRIPTION OF THE DRAWINGS

For a better understanding of the present invention, reference is made to the detailed description of the invention, by way of example, which is to be read in conjunction with the following drawings, wherein like elements are given like reference numerals, and wherein:

FIG. 11 is a screen display of a point list of data was acquired in accordance with a disclosed embodiment of the invention;

DETAILED DESCRIPTION OF THE INVENTION

In the following description, numerous specific details are set forth in order to provide a thorough understanding of the present invention. It will be apparent to one skilled in the art, however, that the present invention may be practiced without these specific details. In other instances, well-known circuits, control logic, and the details of computer program instructions for conventional algorithms and processes have not been shown in detail in order not to obscure the present invention unnecessarily.

Software programming code, which embodies aspects of the present invention, is typically maintained in permanent storage, such as a computer readable medium. In a client-server environment, such software programming code may be stored on a client or a server. The software programming code may be embodied on any of a variety of known media for use with a data processing system. This includes, but is not limited to, magnetic and optical storage devices such as disk drives, magnetic tape, compact discs (CD's), digital video discs (DVD's), and computer instruction signals embodied in a transmission medium with or without a carrier wave upon which the signals are modulated. For example, the transmission medium may include a communications network, such as the Internet. In addition, while the invention may be embodied in computer software, the functions necessary to implement the invention may alternatively be embodied in part or in whole using hardware components such as application-specific integrated circuits or other hardware, or some combination of hardware components and software.

System Architecture

Figure 1:
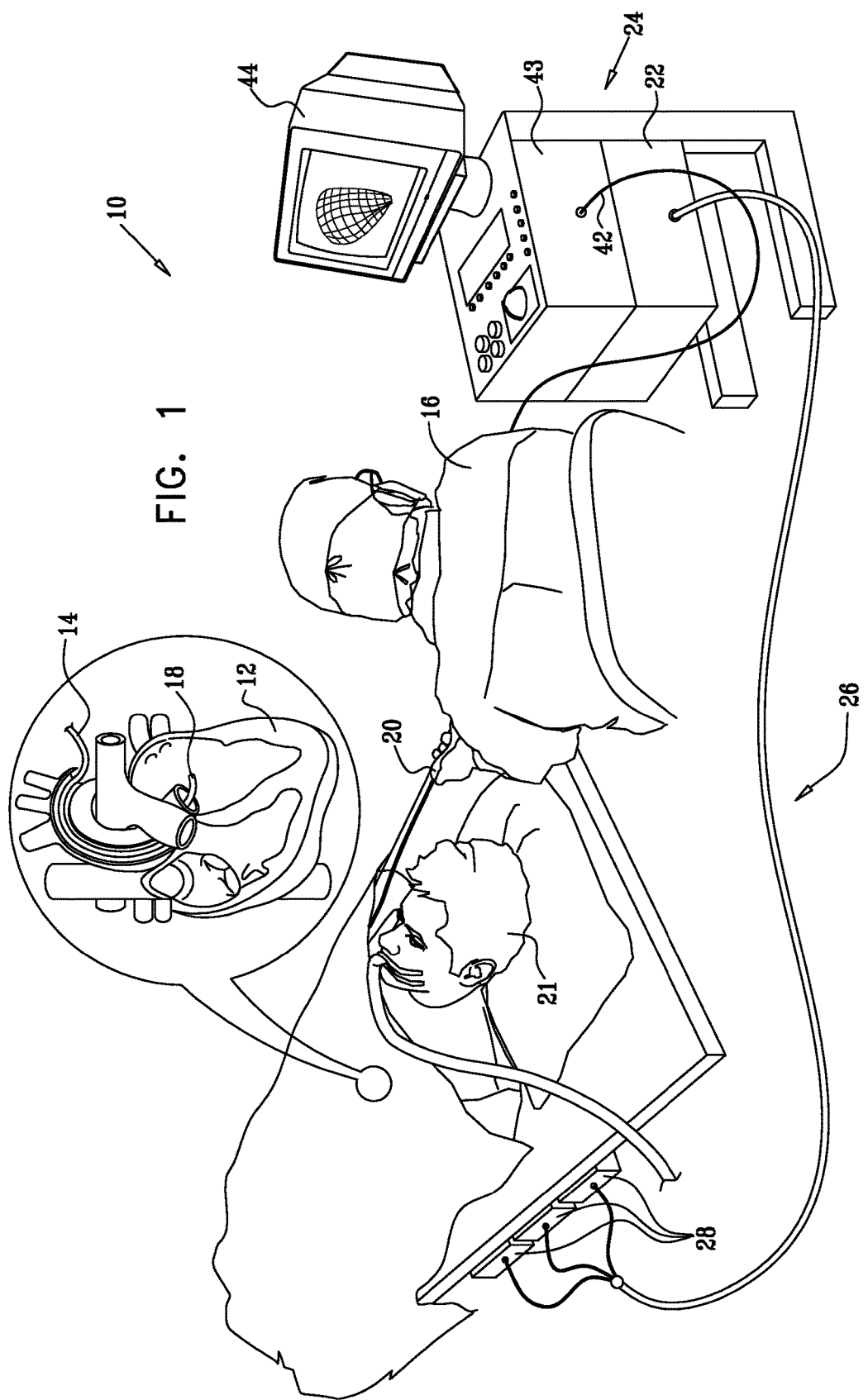
FIG. 1 is a pictorial illustration of a system for detecting areas of abnormal electrical activity and performing ablative procedures on a heart of a living subject in accordance with a disclosed embodiment of the invention.

Turning now to the drawings, reference is initially made to FIG. 1, which is a pictorial illustration of a system 10 for detecting areas of abnormal electrical activity and performing ablative procedures on a heart 12 of a living subject 21 in accordance with a disclosed embodiment of the invention. The system comprises a probe, typically a catheter 14, which is percutaneously inserted by an operator 16, who is typically a physician, through the patient's vascular system into a chamber or vascular structure of the heart. The operator 16 brings the catheter's distal tip 18 into contact with the heart wall at a target site that is to be evaluated. Electrical activation maps are then prepared, according to the methods disclosed in the above-noted U.S. Pat. Nos. 6,226,542, and 6,301,496, and in commonly assigned U.S. Pat. No. 6,892, 091, whose disclosure is herein incorporated by reference.

Areas determined to be abnormal by evaluation of the electrical activation maps can be ablated application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. Alternatively, other known methods of applying ablative energy can be used, e.g., ultrasound energy, as disclosed in U.S. Patent Application Publication No. 2004/0102769, whose disclosure is herein incorporated by reference. The principles of the invention are disclosed with respect to atrial complex fractionated electrograms, but can be applied to all heart chambers, to epicardial as well as endocardial approaches, and to mapping in sinus rhythm, and when many different cardiac arrhythmias are present.

The catheter 14 typically comprises a handle 20, having suitable controls on the handle to enable the operator 16 to steer, position and orient the distal end of the catheter as desired to the ablation. To aid the operator 16, the distal portion of the catheter 14 contains position sensors (not shown) that provide signals to a positioning processor 22, located in a console 24. The catheter 14, may be adapted, mutatis mutandis, from the ablation catheter described in commonly assigned U.S. Pat. No. 6,669,692, whose disclosure is herein incorporated by reference. The console 24 typically contains an ablation power generator 43.

The positioning processor 22 is an element of a positioning subsystem 26 that measures location and orientation coordinates of the catheter 14. Throughout this patent application, the term "location" refers to the spatial coordinates of the catheter, and the term "orientation" refers to its angular coordinates. The term "position" refers to the full positional information of the catheter, comprising both location and orientation coordinates.

In one embodiment, the positioning subsystem 26 comprises a magnetic position tracking system that determines the position and orientation of the catheter 14. The positioning subsystem 26 generates magnetic fields in a predefined working volume its vicinity and senses these fields at the catheter. The positioning subsystem 26 typically comprises a set of external radiators, such as field generating coils 28, which are located in fixed, known positions external to the patient. The coils 28 generate fields, typically electromagnetic fields, in the vicinity of the heart 12.

In an alternative embodiment, a radiator in the catheter 14, such as a coil, generates electromagnetic fields, which are received by sensors (not shown) outside the patient's body.

Some position tracking systems that may be used for this purpose are described, for example, in the above-noted U.S. Pat. No. 6,690,963, and in commonly assigned U.S. Pat. Nos. 6,618,612 and 6,332,089, and U.S. Patent Application Publications 2004/0147920, and 2004/0068178, whose disclosures are all incorporated herein by reference. Although the positioning subsystem 26 shown in FIG. 1 uses magnetic fields, the methods described below may be implemented using any other suitable positioning subsystem, such as systems based on electromagnetic fields, acoustic or ultrasonic measurements.

Figure 2:
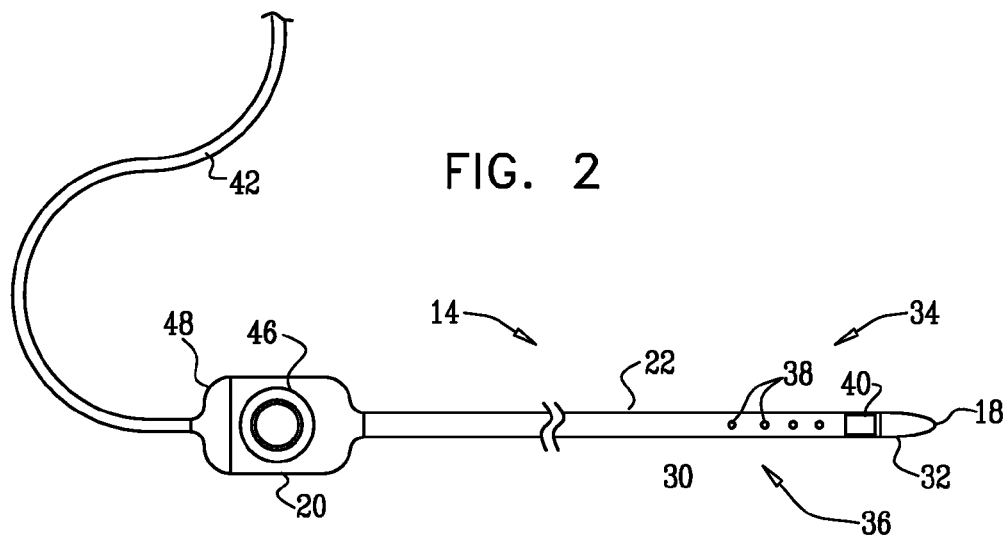
FIG. 2 is a diagram of an embodiment of a catheter for use in the system shown in FIG. 1.

Reference is now made to FIG. 2, which is a diagram of an embodiment of the catheter 14 for use in the system 10 (FIG. 1). The catheter 14 is a mapping and therapeutic delivery catheter for insertion into the human body, and into a chamber of the heart 12 (FIG. 1). The catheter shown is exemplary; many other types of catheters can be used as the catheter 14. The catheter 14 includes a body 30. An electrode 32 is at a distal portion 34 disposed for measuring the electrical properties of the heart tissue. The electrode 32 is also useful for sending electrical signals to the heart for diagnostic purposes, e.g., for electrical mapping, and/or for therapeutic purposes, e.g., for ablating defective cardiac tissue. The distal portion 34 further includes an array 36 of non-contact electrodes 38 for measuring far field electrical signals in the heart chamber. The array 36 is a linear array in that the non-contact electrodes 38 are linearly arranged along the longitudinal axis of the distal portion 34. The distal portion 34 further includes at least one position sensor 40 that generates signals used to determine the position and orientation of the distal tip 18 within the body. The position sensor 40 is preferably adjacent to the distal tip 18. There is a fixed positional and orientational relationship of the position sensor 40, the distal tip 18 and the electrode 32.

The position sensor 40 transmits, in response to the fields produced by the positioning subsystem 26 (FIG. 1), position-related electrical signals over a cable 42 running through the catheter 14 to the console 24. Alternatively, the position sensor 40 in the catheter 14 may transmit signals to the console 24 over a wireless link, as described in U.S. Patent Application Publication Nos. 2003/0120150 and 2005/0099290, the disclosures of which are herein incorporated by reference. The positioning processor 22 then calculates the location and orientation of the distal portion 34 of the catheter 14 based on the signals sent by the position sensor 40. The positioning processor 22 typically receives, amplifies, filters, digitizes, and otherwise processes signals from the catheter 14. The positioning processor 22 also provides a signal output to a display 44 that provides a visual indication of the position of the distal portion 34 and/or the distal tip 18 of the catheter 14 relative to the site chosen for ablation.

The handle 20 of the catheter 14 includes controls 46 to steer or deflect the distal portion 34, or to orient it as desired.

The cable 42 comprises a receptacle 48, which connects to the handle 20. The receptacle 48 is preferably configured to receive catheters of a specific model, and preferably includes user-evident identification of the specific model. One of the advantages in using the cable 42 is the ability to connect different models and types of catheters, such as those catheters having different handle configurations, to the same console 24 (FIG. 1). Another advantage in having a separate cable 42 is in the fact that it does not come into contact with patients, so that it is possible to reuse the cable 42 without sterilization. The cable 42 further contains one or more isolation transformers (not shown), which electrically isolate the catheter 14 from the console 24. The isolation transformers may be contained in the receptacle 48. Alternatively, isolation transformers may be contained in the system electronics of the console 24.

Referring again to FIG. 1, the system 10 can be realized as the above-mentioned CARTO XP EP Navigation and Ablation System, suitably modified to execute the procedures described herein.

Electrical Mapping

Figure 3:
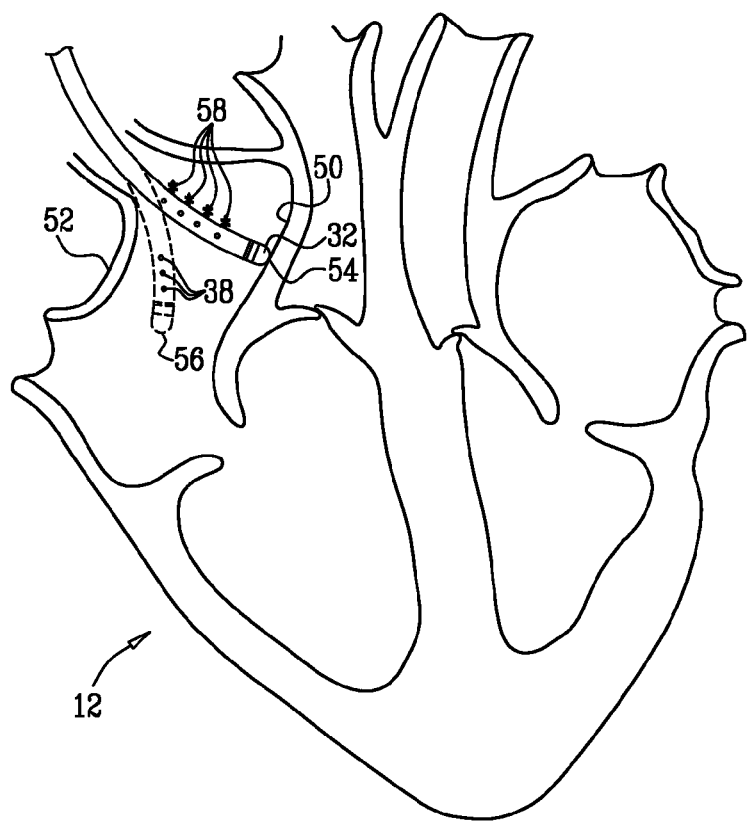
FIG. 3 is a diagram depicting the distal end of a catheter in contact with the endocardial surface of the right atrium of a heart, in accordance with a disclosed embodiment of the invention.

Using the system 10 (FIG. 1), an electrical activation map of a chamber of the heart 12 can be generated using the methods described in the above-noted U.S. Pat. No. 6,892,091. A summary of one of these methods, modified according to the aspects of the present invention, will facilitate an understanding of the invention. Reference is now made to FIG. 3, which depicts the distal end of the catheter 14 in contact with an endocardial surface 50 of the right atrium 52 of the heart 12, in accordance with a disclosed embodiment of the invention. The electrode 32 is maintained in contact with the endocardial surface 50 at a current contact point 54 throughout at least an entire cardiac cycle. During this time, location information, is continuously measured by the position sensor 40 (FIG. 2), while electrical information, preferably, voltage (as a function of time), is measured by the electrode 32 and each of the non-contact electrodes 38 in the array 36 (FIG. 2).

After the above electrical and location information is collected at the contact point 54, the electrode 32 is contacted with another contact point, e.g., a contact point 56 elsewhere on the endocardial surface of the right atrium 52.

Points 58, shown as asterisks, represent the locations of the non-contact electrodes 38 while the electrode 32 was in contact with the contact point 54.

The electrode 32 is advanced over a plurality of contact points on the cardiac chamber's endocardial surface. Location and electrical information is acquired while the contact electrode is in contact with each of the contact points. Typically, the above-described contacting and information acquisition steps are effected at between 5-15 such contact points. Since there are multiple non-contact electrodes 38, the total number of points used to acquire data in a chamber may be 160 points or more. The resultant location and electrical information acquired from the electrode 32 and the non-contact electrodes 38 at each of acquisition step provides the basis for generating an electrical map of the heart chamber.

The location of the contact electrodes at each of the contact points may be used to define the geometric map of the cardiac chamber. While not actually contacting the cardiac surface, the totality of the non-contact electrode locations defines a "cloud" of space, which represents a minimum chamber volume. These non-contact locations may be used, alternatively, or together with the location of the electrode 32 at each of the contact points, to define the chamber geometry.

It is preferable to use a reference location sensor to correct for patient movement during the procedure or to movement of the heart due to patient breathing. One method of obtaining a location reference is by the use of a reference catheter (not shown) containing a reference location sensor elsewhere in the heart. Alternatively, a reference location sensor may be contained in a pad that might be attached external to the patient, for example on the back of the patient. In either case, locations determined by the sensors contained in the mapping catheter may be corrected for patient movement with the reference sensors.

A preferred method for generating the electrical map of the heart from the acquired location and electrical information is described in the above noted U.S. Pat. No. 6,226,542. Briefly, an initial, generally arbitrary, closed 3-dimensional curved surface (also referred to herein for brevity as a curve) is defined in a reconstruction space in the volume of the sampled points. The closed curve is roughly adjusted to a shape, which resembles a reconstruction of the sampled points. Thereafter, a flexible matching stage is preferably repeatedly performed one or more times in order to bring the closed curve to accurately resemble the shape of the actual volume being reconstructed. The 3-dimensional surface may be rendered to a video display or other screen for viewing by a physician or other user of the map.

The initial closed curved surface preferably encompasses substantially all the sampled points or is interior to substantially all the sampled points. However, it is noted that any curve in the vicinity of the sampled points is suitable. Preferably, the closed three-dimensional curved surface comprises an ellipsoid, or any other simple closed curve. Alternatively, a non-closed curve may be used, for example, when it is desired to reconstruct a single wall rather than the entire volume.

A grid of a desired density is defined on the curve. For each of the points on the grid, a vector is defined, which is dependent on the displacement between one or more of the grid points and one or more of the measured locations on the cardiac surface. The surface is adjusted by moving each of the grid points in response to the respective vector, so that the reconstructed surface is deformed to resemble the actual configuration of the cardiac chamber. The grid preferably divides the curved surface into quadrilaterals or any other polygons such that the grid evenly defines points on the curve. Preferably, the grid density is sufficient such that there are generally more grid points than sampled points in any arbitrary vicinity. Further preferably, the grid density is adjustable according to a desired compromise between reconstruction accuracy and speed.

CFAE Identification

CFAE's are nominally defined as areas that exhibit one of the following characteristics. In practice, a user or operator may vary these characteristics, according to his experience and judgement with respect to a particular patient:

(1) areas of the atrium that have fractionated electrograms composed of two deflections or more and/or perturbation of the baseline with a continuous deflection of a prolonged activation complex over a 10-sec recording period; or (2) areas of the atrium where the electrogram has a very short cycle length (e.g., 120 ms) averaged over a 10 second recording period. The recording period is not critical, and recording intervals of other lengths may be used.

In aspects of the current embodiment the number of intervals between complexes is represented. However, this not limiting, and other types of information derived from data manipulation may form a basis for representing the number and characteristics of complexes.

Figure 4:
FIG. 4 is a group of exemplary electrograms illustrating CFAE's, which can be automatically identified according to a disclosed embodiment of the invention.

Reference is now made to FIG. 4, which are exemplary electrograms illustrating CFAE's, which can be automatically identified according to a disclosed embodiment of the invention. These electrograms are extracted from Nademanee et al., noted above. One type of CFAE is illustrated by an electrogram 60, which describes a continuous, prolonged activation complex over the posterior septal area. Reference tracings from leads II and V2 are indicated by graphs 62, 64, respectively. Another type of CFAE is indicated by an electrogram 66, taken at the roof of the left atrium. The cycle length is much shorter than that of the remainder of the atrium. A reference tracing from lead aVF is indicated by a graph 68.

In order to identify CFAE's, fractionated complex duration mapping tools were constructed as a modification of the system software of the above-noted CARTO XP EP Navigation and Ablation System. Although the software is described with reference to this particular system, the invention is not limited to the CARTO XP EP Navigation and Ablation System, but can be applied to many other electrical mapping systems by those skilled in the art.

Complex Duration Detection

Figure 5:
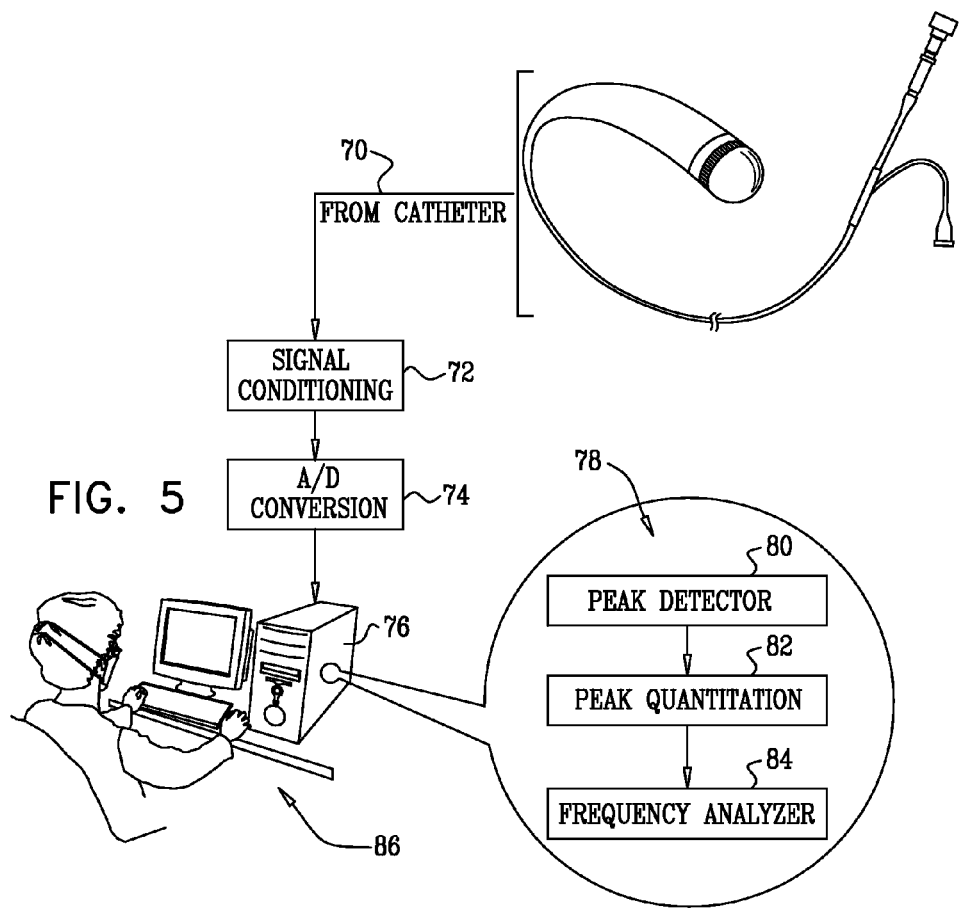
FIG. 5 is a block diagram illustrating a subsystem of the system shown in FIG. 1, in accordance with a disclosed embodiment of the invention.

Reference is now made to FIG. 5, which is a block diagram illustrating a subsystem 86 that comprises aspects of the system 10 (FIG. 1), in accordance with a disclosed embodiment of the invention. The subsystem 86 processes signals 70 from the catheter 14 indicative of cardiac electrical activity. In a signal conditioning block 72, the signals under go conventional signal processing and conditioning, e.g., amplification, and filtering. A/D conversion is accomplished in block 74. The conditioned signals then are subjected to analysis in a processor 76, which can be realized as a general purpose computer. Typically, the functions represented by the blocks 72, 74, and the processor 76 are incorporated in the console 24 (FIG. 1).

The processor 76 includes a memory 78 that contains objects corresponding to the functional blocks depicted therein. Alternatively, the objects shown in the memory 78 can be implemented as dedicated hardware modules, or as conventional types of firmware.

In order to detect CFAE's, the signals 70 are analyzed for the presence of peaks meeting predetermined criteria of magnitude and frequency. Essentially, signal data is automatically analyzed to identify voltage peaks having amplitudes within a predefined voltage range, and to identify peak-to-peak intervals between the identified voltage peaks that occur within a predefined time range. This is accomplished using a peak detection module 80, a peak quantitation module 82, and a frequency analyzer 84, all of which are well known in the art, and will not be further described herein. Indeed, all of the functions indicated in the memory 78 are incorporated in the above-referenced CARTO XP EP Navigation and Ablation System, and can be invoked by system and application software.

Operation

Based on a default or user-configured definition of a CFAE complex, the subsystem 86 detects qualifying peaks that meet predefined voltage criteria, identifies the number of intervals between adjacent qualifying peaks, and the duration between the intervals. Each pair of qualifying peaks separated by a predefined interval range establishes two CFAE complexes. The system thus identifies CFAE complexes within a range of amplitude and duration values. As will be seen from the following description, functional maps representing the spatial distribution and the characteristics of CFAE complexes are generated. The maps may be displayed and compared with maps developed from another study for the same patient or a different patient. This enables the user to compare data, diagnostic and therapeutic strategies. Several types of functional maps may be generated by the subsystem 86.

Figure 6:
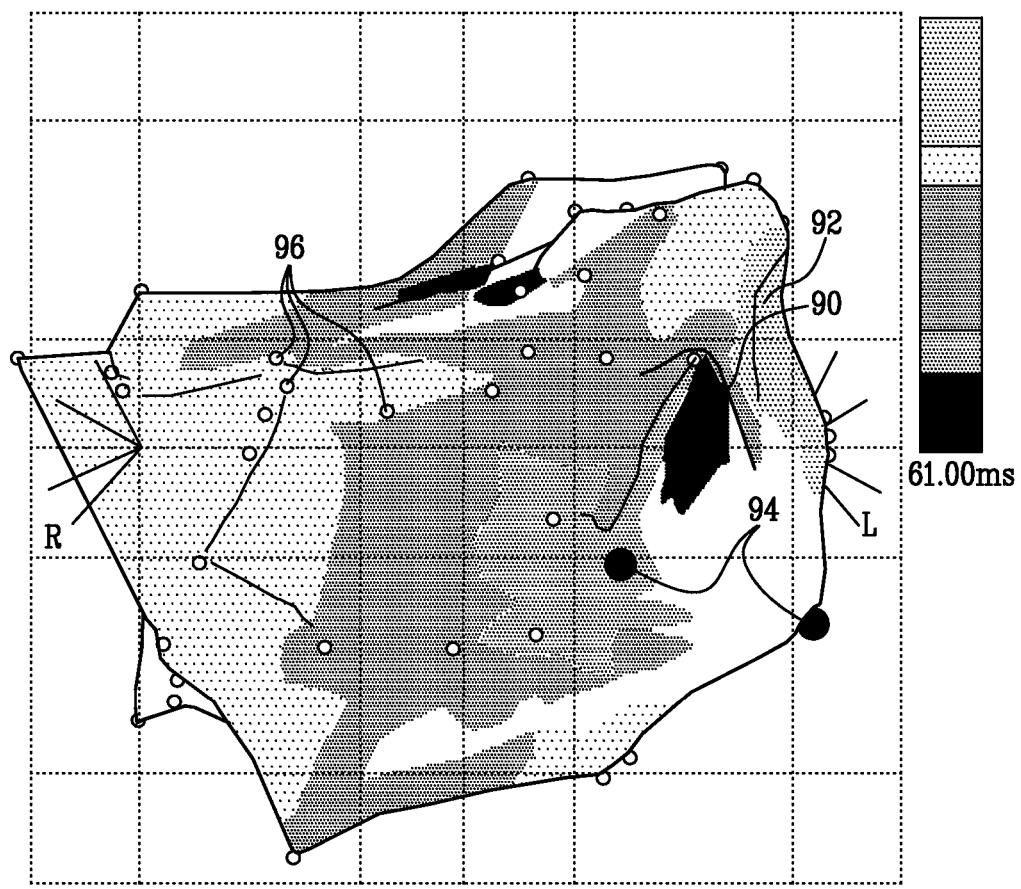
FIG. 6 is a functional map of the left atrium in which a color scale indicates the average cycle length between identified CFAE's, in accordance with a disclosed embodiment of the invention.

Reference is now made to FIG. 6, which is a functional map of the left atrium of a heart in which a color scale indicates the average cycle length between identified CFAE's, in accordance with a disclosed embodiment of the invention. A color scale bar indicates the maximum and minimum durations of the detected time intervals. A user-defined fill threshold is established for the area color representation by each mapping point. This prevents wide areas having no real data from being colored. In FIG. 6, an area 88 did not meet the requisite threshold and remains uncolored. An area 90 corresponds to a region in which the average interval between complexes is about 61 ms. In a relatively small area 92, the average interval is much longer, about 116 ms. Circles 94 are confidence level tags. By default, three types of color-coded confidence level tags are displayed, corresponding to measurements of seven, four, and two intervals between CFAE's during the examination. The circles 94 correspond to the intermediate confidence level of four measured intervals between CFAE's. Mapping points 96 are indicated as dots scattered about the map.

Figure 7:
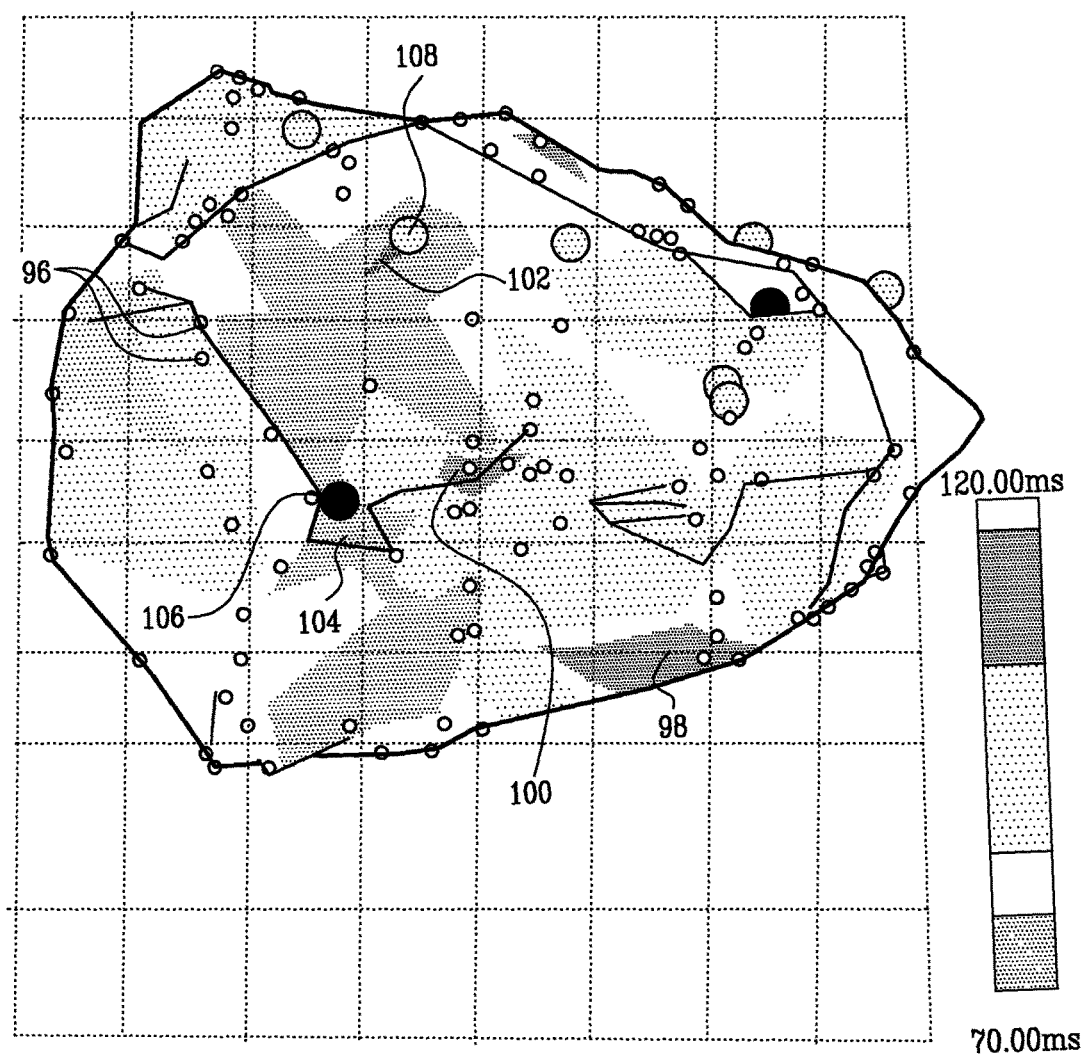
FIG. 7 is a functional map of the left atrium in which a color scale indicates the shortest interval between identified CFAE's for each acquired point, in accordance with a disclosed embodiment of the invention.

Reference is now made to FIG. 7, which is a functional map of the left atrium of a heart in which a color scale indicates the shortest interval between identified CFAE's for each acquired point in accordance with a disclosed embodiment of the invention. Numerous mapping points 96 are shown. Additionally or alternatively, confidence tags or textual labels (not shown) may indicate confidence levels on the map. Areas 98, 100 correspond to long intervals between CFAE's, while areas 102, 104 correspond to short intervals. Circles 106, 108 represent regional color-coded confidence levels.

Figure 8:
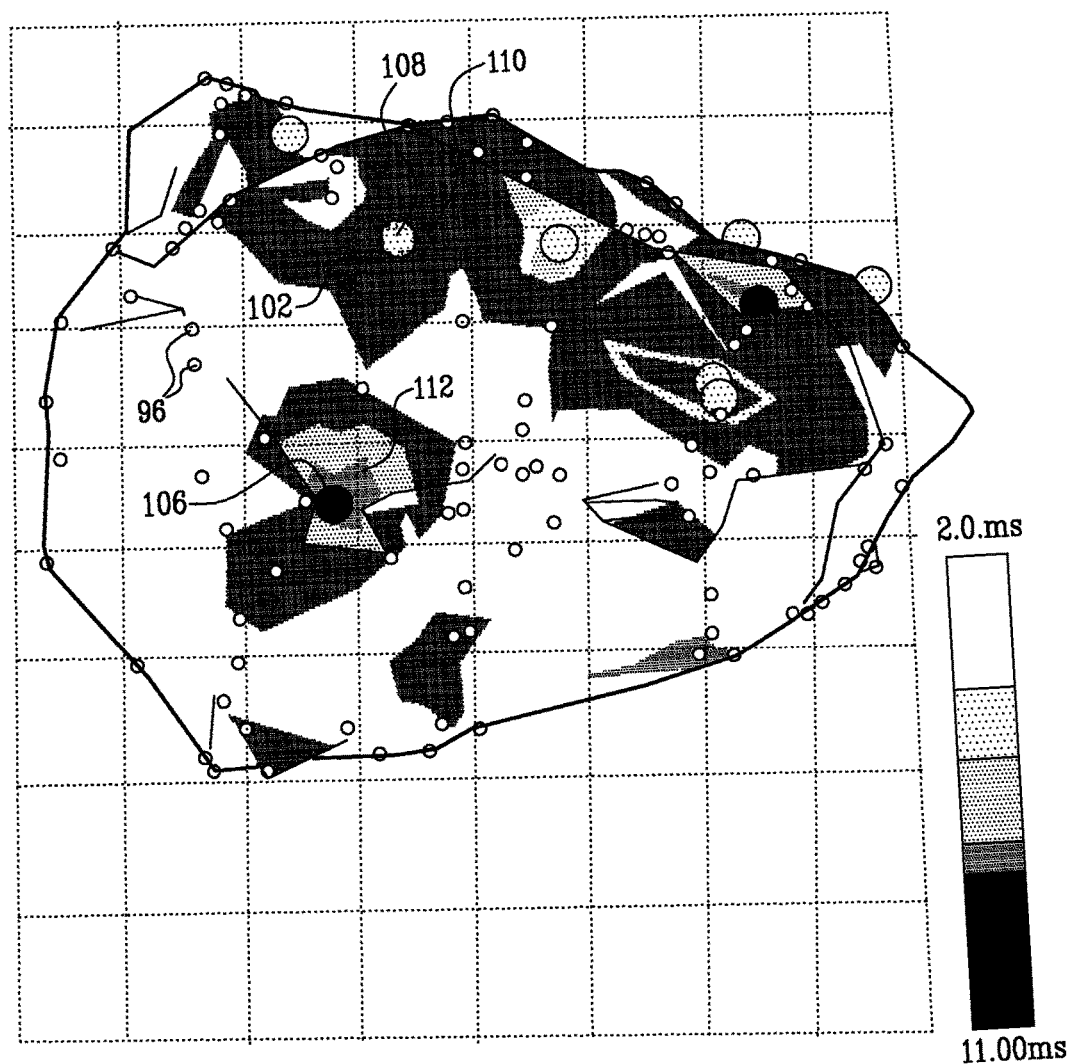
FIG. 8 is an interval confidence map of the left atrium, in accordance with a disclosed embodiment of the invention.

Reference is now made to FIG. 8, which is an interval confidence map of the left atrium shown in FIG. 7, in accordance with a disclosed embodiment of the invention. A color scale indicates the number of repeated CFAE's detected, that is the number of qualifying intervals between adjacent complexes for each acquired point. An area 110 has a relatively large number of repeated complexes, and is color-coded according to the number of complexes. An area 112 shows very few repeated CFAE's. The circles 106, 108 are shown, corresponding with those on FIG. 7.

Thus, on the shortest interval display of FIG. 7, the confidence levels of the interval data can be immediately determined by reference to the color coding of the circles 106, 108, which are essentially excerpts of the more detailed confidence level map of FIG. 8.

In all of the aforementioned functional maps, the default confidence level coding may be modified by the user, and tags may be optionally added to points that meet user-defined confidence levels.

Figure 9:
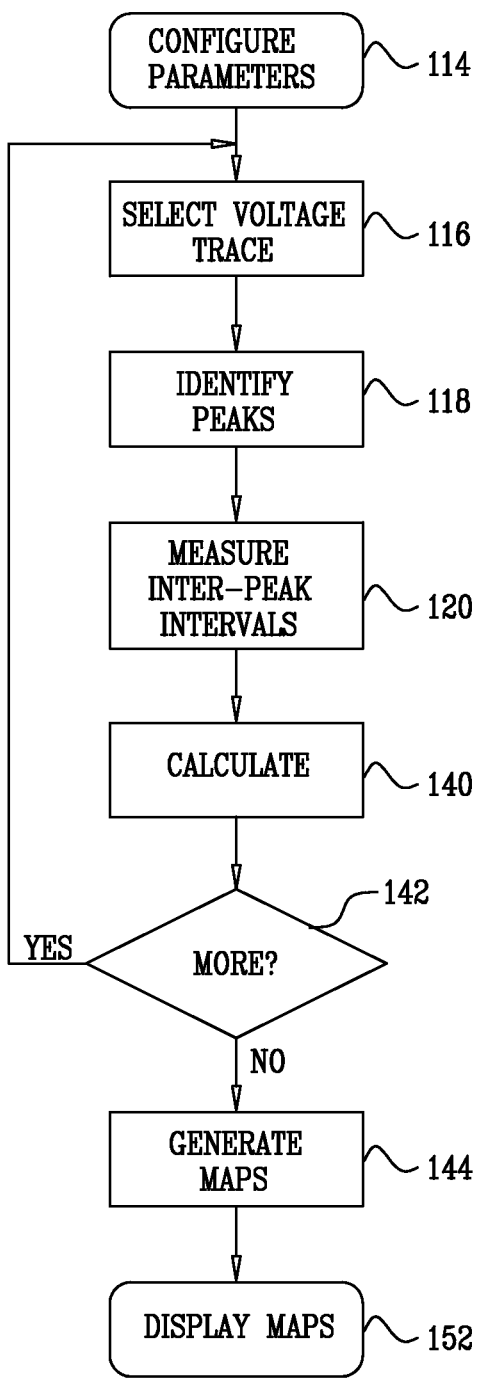
FIG. 9 is a flow chart illustrating a method of CFAE detection, in accordance with a disclosed embodiment of the invention.

Referring again to FIG. 5, the processor 76 executes a detection algorithm for each mapped point or pair of mapped points. Reference is now made to FIG. 9, which is a flow chart illustrating a method of CFAE detection, in accordance with a disclosed embodiment of the invention. It is assumed that a patient study is concurrently underway or has been completed, and that voltage tracing records have been memorized. Additionally or alternatively, anatomical maps may be produced and superimposed or co-displayed with functional CFAE maps. At initial step 114, parameters are set. Suitable default parameters for peak detection and peak duration are given in Table 1, all of which are user-modifiable.

TABLE 1

| Parameter | Default Value | Remarks |
|---|---|---|
| Minimum Threshold | 0.05 mV | |
| Maximum Threshold | 0.15 mV | |
| Minimum Duration | 70 ms | |
| Maximum Duration | 120 ms | |
| Mapping Mode | Bipolar | |
| "Peak Above" | Enabled | When enabled, peaks that exceed or fall below the minimum and maximum thresholds are included in interval calculations |
| High Confidence Level | >=7 | Greater than 7 intervals detected between CFAE's |
| Medium Confidence Level | >=4 | |
| Low Confidence Level | >=2 | Fewer than 2 intervals are ignored. |

Next, at step 116 a voltage trace record is selected from the available measurements.

Next, at step 118, using conventional signal processing and conditioning methods, the tracing is converted to digital form. The digitized record is scanned and all peaks detected in which the voltages lie between the minimum and maximum thresholds. Furthermore, when the "peak above" mode is set, peaks in which voltage excursions exceed the maximum threshold or fall below the minimum threshold are included in the algorithm calculation—hence ignoring high voltage tracings and mistakenly.

Next, at step 120, time intervals are measured between peaks that were identified in step 118. The number of peak-to-peak intervals that fall between the minimum and maximum duration is recorded as identified CFAE complexes. The peak times, voltage values, and peak-to-peak interval data are stored, typically in an array for convenient recall during map generation. The peaks may be identified and characterized on an annotation display.

Figure 10:
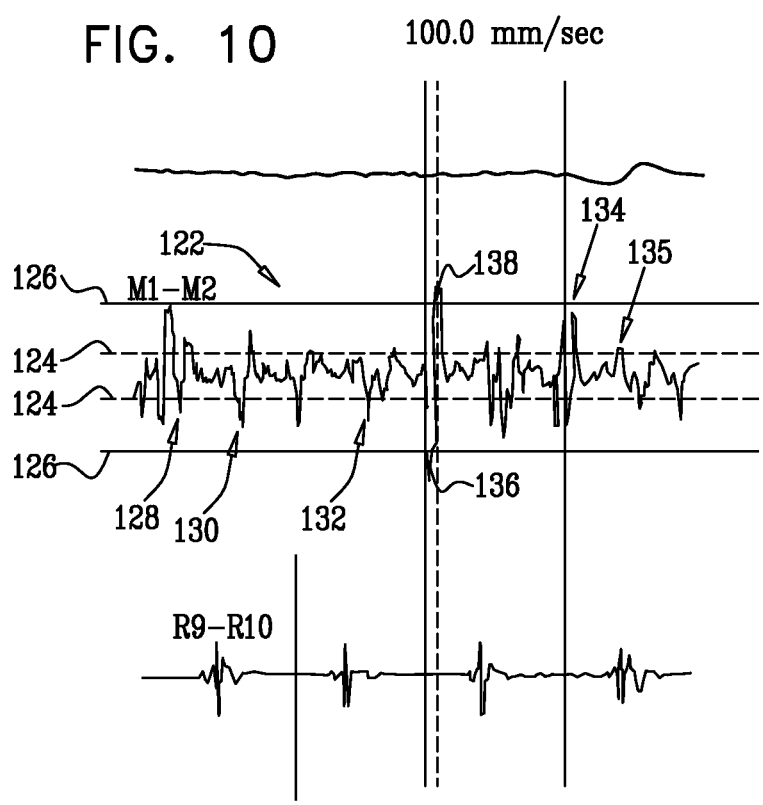
FIG. 10 is a screen display illustrating a tracing, in which peaks and peak-to-peak intervals identified during the performance of the method shown in FIG. 9 have been annotated, in accordance with a disclosed embodiment of the invention.

Reference is now made to FIG. 10, which is a screen display of an annotation viewer of the subsystem 86 (FIG.

5) illustrating a tracing 122, in which peaks and peak-to-peak intervals identified during the performance of steps 118, 120 (FIG. 9) have been annotated in accordance with a disclosed embodiment of the invention. Ranges between minimum and maximum voltage thresholds are framed by parallel lines 124, 126, respectively. Five representative qualifying peaks, all having voltage amplitudes within the voltage range defined by the lines 124, 126, are indicated by vertical arrows 128, 130, 132, 134, 135. Two peaks 136, 138 exceed the ranges defined by the minimum and maximum voltage thresholds, but are included in the calculations if the "Peak Above" option is enabled. For example, in the tracing 122, two CFAE's separated by a short cycle are identified by the arrows 128, 130.

Referring again to FIG. 9, at step 140 calculations of the average interval, shortest interval, and spatial confidence level distribution are made and recorded.

Control now proceeds to decision step 142, where it is determined if more tracings remain to be evaluated. If the determination at decision step 142 is affirmative, then control returns to step 116.

If the determination at decision step 142 is negative, then control proceeds to step 144. Using the data calculated in steps 118, 120, CFAE maps are generated, examples of which were presented in FIG. 6, FIG. 7, and FIG. 8. Construction of such functional maps may be accomplished using known methods; for example, those taught in the above-noted U.S. Pat. Nos. 6,226,542, and 6,301,496. The user may adjust the default parameters (Table 1) used for coloring interval confidence levels maps. The user may set a flag that determines whether confidence level tags are to be displayed or hidden. As noted above, in one embodiment, such tags may appear as colored circles, the color of which indicates the confidence level of the pseudo-colored area over which it appears.

Reference is now made to FIG. 11, which is a screen display of a point list of data that may be co-displayed with any of the above-noted CFAE maps in accordance with a disclosed embodiment of the invention. For each mapped data point, the shortest complex interval (SCI) between two consecutive CFAE's is shown in a column 146. The interval confidence level (ICL) of the point is presented in a column 148. If there are two or more adjacent CFAE complexes in the signal, the column 148 displays the number of CFAE intervals. A column 150 show the type of confidence level tag (CLT) applied to the point. Although not present in FIG. 11, if an average complex interval map is being co-displayed, the point list would also include an indication of the average complex interval for all the CFAE complex intervals in the signal.

Referring again to FIG. 9, at final step 152, the user may cause the CFAE maps that were generated to be displayed in many combinations, and may create windows in which displays from other studies appear for comparison with the current study. Cardiac tissue associated with the complex fractionated electrograms may be ablated conventionally.

Alternate Embodiment 1

In this embodiment, the first criterion described in the section entitled CFAE Identification is applied using the system 10 (FIG. 1). This is done by recording for longer periods, e.g., 50 sec, and detecting two CFAE complexes within a 10 second interval at a point. Alternatively, it is also possible to detect a prolonged perturbation of the baseline that exceeds 10 seconds by recording an average baseline and scanning the data for prolonged deviations.

Alternate Embodiment 2

Figure 12:
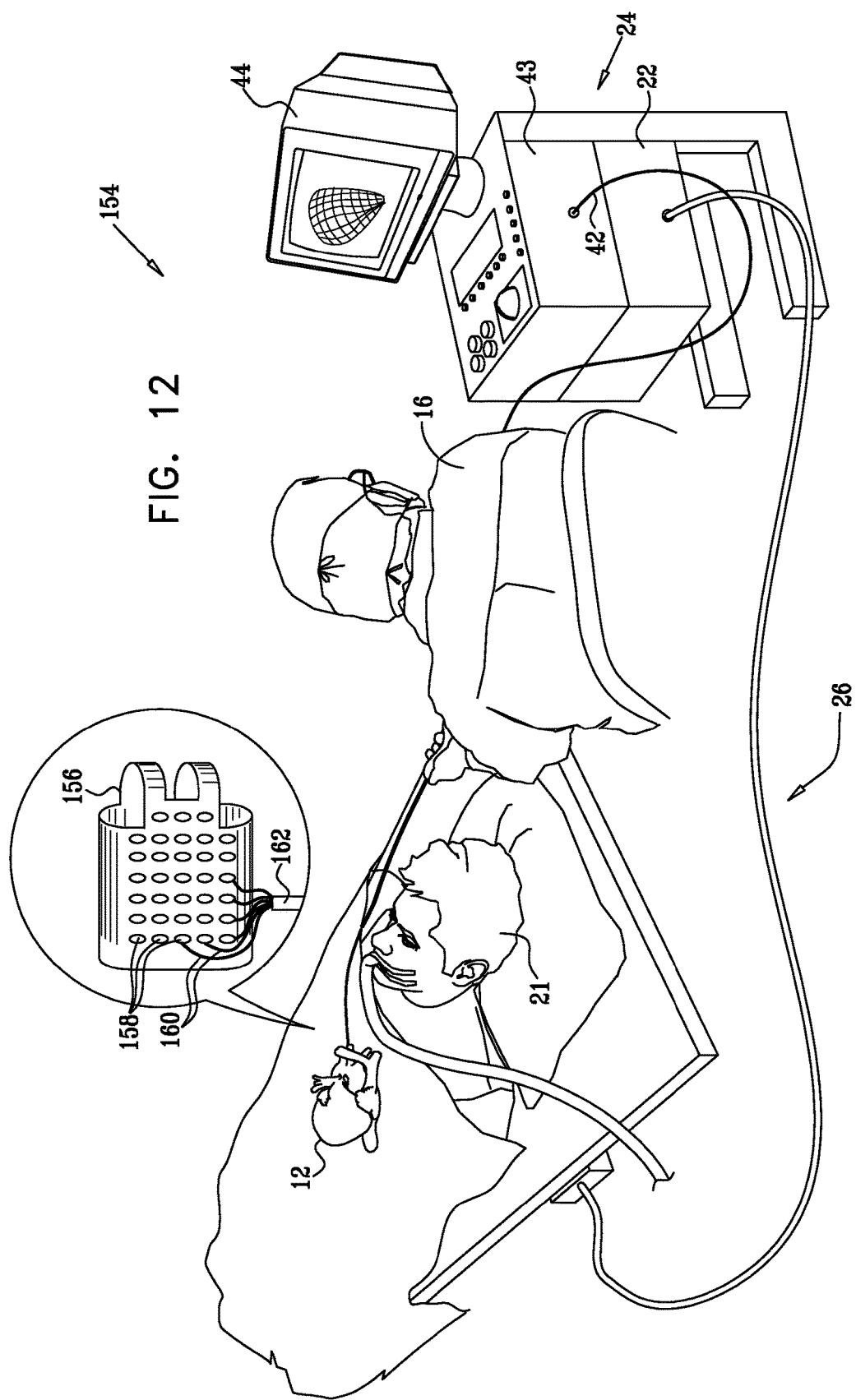
FIG. 12 is an illustration of a system for detecting areas of abnormal electrical activity and performing ablative procedures on a heart of a living subject in accordance with an alternate embodiment of the invention.

Reference is now made to FIG. 12, which is an illustration of a system 154, which is constructed and operative in accordance with an alternate embodiment of the invention. The system 106 is similar to the system 10 (FIG. 1). However the processor 22 now contains electrical circuitry for impedance detection, as described in U.S. patent application Ser. No. 11/030,934, filed Jan. 7, 2005, which is assigned to the assignee of the present patent application and whose disclosure is incorporated herein by reference. However the subject 21 is now clothed in a torso vest 156 that has a plurality of electrodes 158, typically between about 125 and 250 electrodes, which are disposed within the torso vest 156 to provide measurements of electrical potentials over the anterior, posterior and lateral aspects of the torso of the subject 21. The electrodes 158 are connected via leads 160 and a cable 162 to the processor 22. The processor 22 is modified for receiving and processing data from the torso vest 156.

The system is modified to generate, based on impedance measurements between a small number of endocardial points and the electrodes 158, a multidimensional matrix of coefficients. The inverse of the matrix is then estimated, as described in U.S. Patent Application Publication No. 2003/0120163 (Yoram Rudy et al.), and in U.S. Provisional Application No. 60/824,680, filed Sep. 6, 2006, and entitled "Correlation of Endocardial and Epicardial Maps", whose disclosures are herein incorporated by reference. The inverse matrix may correspond to a map of epicardial or endocardial electrical conductances.

Figure 13:
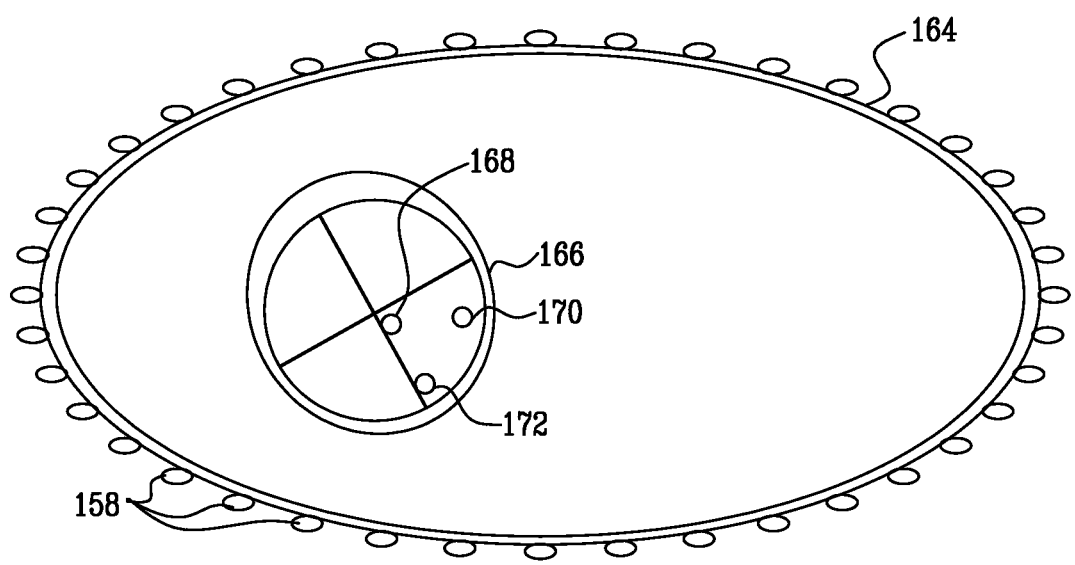
FIG. 13 is a simplified sectional view of a thorax showing a torso vest and electrodes in accordance with an alternate embodiment of the invention.

Reference is now made to FIG. 13, which is a simplified sectional view of a thorax 164 showing the torso vest 156, and the electrodes 158 distributed about the thorax, in accordance with a disclosed embodiment of the invention.

FIG. 13 also shows a right atrium 166, and includes three endocardial points 168, 170, 172. As explained below, impedance measurements are made between catheter electrodes positioned at the endocardial points 168, 170, 172 and the electrodes 158. In some applications, impedances may also be measured between epicardially positioned electrodes (not shown in FIG. 13) and the electrodes 158.

Using the matrix and the other above-described features of the processor 22 and the positioning subsystem 26 to locate the points 168, 170, 172, and by measuring conductances at different points in the cardiac cycle, the CFAE criteria are applied as described above for identification of CFAE's at the points 168, 170, 172. Such points, which may be non-invasively identified in the same or in a subsequent session using a pre-established matrix, become candidate locations for ablation in a subsequent session.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method for mapping abnormal electrical activity in a heart of a living subject, comprising the steps of:
   providing a catheter comprising an electrode distally disposed thereon;
   inserting said catheter into said heart;
   using said catheter and obtaining electrical signal data from respective locations of said heart using said electrode;

providing a subsystem comprising:
- (i) a peak detector module configured to identify voltage peaks having amplitudes within a predefined voltage range from said electrical signal data provided by said electrode of said catheter,
- (ii) a peak quantitation module configured to identify peak-to-peak intervals between said identified voltage peaks that occur within a predefined time range from said electrical signal data provided by said electrode of said catheter, and
  - wherein said subsystem is configured to automatically analyze said signal data to identify complex fractionated electrograms therein using said identified peak-to-peak intervals between said identified voltage peaks that occur within a predefined time range; and displaying on a display information derived from said signal data indicative of a spatial distribution of said complex fractionated electrograms in said heart.

2. The method according to claim 1, wherein said step of obtaining electrical signal data comprises the steps of:
- wherein the catheter further comprises a position sensor distally disposed thereon;
- contacting a surface of said heart using the catheter; and
- measuring electrical signals at said respective locations via said electrode and obtaining location information from said position sensor from at least one point on said surface.

3. The method according to claim 2, wherein said step of measuring electrical signals is performed using a unipolar electrode.

4. The method according to claim 2, wherein step of measuring electrical signals is performed using a bipolar electrodes.

5. The method according to claim 2, wherein said surface is an endocardial surface.

6. The method according to claim 1, wherein said respective locations are at an atrium of said heart.

7. The method according to claim 1, wherein said respective locations are at a ventricle of said heart.

8. The method according to claim 1, wherein at least a portion of said respective locations are on an endocardial surface of said heart.

9. The method according to claim 1, wherein at least a portion of said respective locations are on an epicardial surface of said heart.

10. The method according to claim 1, wherein obtaining electrical signal data from said respective locations of said heart comprises the steps of:
- disposing multiple electrodes on an external surface of said subject;
- detecting electrical signals from said heart using said multiple electrodes; and
- applying said electrical signals to a pre-established impedance matrix to identify said respective locations.

11. The method according to claim 1, wherein displaying information comprises constructing a functional map of said heart that is coded according to average durations of said complex fractionated electrograms.

12. The method according to claim 1, wherein displaying information comprises constructing a functional map of said heart that is coded according to shortest complex durations of said complex fractionated electrograms.

13. The method according to claim 1, wherein displaying information comprises constructing a functional map of said heart that is coded according to numbers of said complex fractionated electrograms detected in said respective locations.

14. The method according to claim 1, further comprising the steps of ablating cardiac tissue associated with said complex fractionated electrograms.

15. A computer software product for use with an apparatus comprising a catheter having an electrode distally disposed thereon configured to obtain electrical signal data from respective locations of said heart using said electrode and a subsystem, wherein the apparatus is configured to map electrical activity in a heart of a living subject, and wherein the subsystem includes a tangible computer-readable medium in which;
- computer program instructions are stored, which instructions, when read by a computer, cause the computer to:
  - store electrical signal data from respective locations of said heart;
  - automatically analyze said signal data to identify complex fractionated electrograms therein using (i) a peak detector module configured to identify voltage peaks having amplitudes within a predefined voltage range from said electrical signal data provided by said electrode of said catheter, and (ii) a peak quantitation module configured to identify peak-to-peak intervals between said identified voltage peaks that occur within a predefined time range from said electrical signal data provided by said electrode of said catheter, and; and
  - output information to a display that is indicative of a spatial distribution of said complex fractionated electrograms in said heart.

16. The computer software product according to claim 15, wherein said computer is further instructed to construct a functional map of said heart that is coded according to average durations of said complex fractionated electrograms.

17. The computer software product according to claim 15, wherein said computer is further instructed to construct a functional map of said heart that is coded according to shortest complex durations of said complex fractionated electrograms.

18. The computer software product according to claim 15, wherein said computer is further instructed to construct a functional map of said heart that is coded according to numbers of said complex fractionated electrograms detected in said respective locations.

19. An apparatus for mapping electrical activity in a heart of a living subject, comprising:
- a catheter comprising an electrode distally disposed thereon configured to obtain electrical signal data from respective locations of said heart using said electrode;
- a subsystem comprising:
  - (i) a peak detector module configured to identify voltage peaks having amplitudes within a predefined voltage range from said electrical signal data provided by said electrode of said catheter,
  - (ii) a peak quantitation module configured to identify peak-to-peak intervals between said identified voltage peaks that occur within a predefined time range from said electrical signal data provided by said electrode of said catheter, and
  - (iii) a processor configured to to automatically analyze said signal data using said identified peak-to-peak intervals between said identified voltage peaks that occur within a predefined time range to identify complex fractionated electrograms therein and to construct a functional map of said heart that is indicative of a spatial distribution of said complex fractionated electrograms in said heart; and a display linked to said processor for displaying said functional map.

20. The apparatus according to claim 19, wherein said functional map is coded by said processor according to average durations of said complex fractionated electrograms.

21. The apparatus according to claim 19, wherein said functional map is coded by said processor according to shortest complex durations of said complex fractionated electrograms.

22. The apparatus according to claim 19, wherein said functional map of said heart coded by said processor according to numbers of said complex fractionated electrograms detected in said respective locations.

* * * * *